United States Patent [19]
Weaver

[11] Patent Number: 5,893,849
[45] Date of Patent: *Apr. 13, 1999

[54] CAUTERY MEDICAL INSTRUMENT

[75] Inventor: Drew D. Weaver, Sandy, Utah

[73] Assignee: MegaDyne Medical Products, Inc., Draper, Utah

[*] Notice: This patent is subject to a terminal disclaimer.

[21] Appl. No.: 08/864,257

[22] Filed: May 28, 1997

Related U.S. Application Data

[63] Continuation of application No. 08/200,541, Feb. 22, 1994, Pat. No. 5,697,926, which is a continuation of application No. 07/991,974, Dec. 17, 1992, abandoned.

[51] Int. Cl.$^6$ .................................................. A61B 17/36
[52] U.S. Cl. .................................. 606/41; 606/39; 606/45
[58] Field of Search ................................. 606/39, 40, 41, 606/45, 49

[56] References Cited

U.S. PATENT DOCUMENTS 5,697,926 12/1997 Weaver .................................. 606/41

*Primary Examiner*—Michael Peffley
*Assistant Examiner*—Sonya Harris-Ogugua
*Attorney, Agent, or Firm*—John L. Sigalos

[57] ABSTRACT

A cautery instrument having a first predetermined region for contact with flesh or tissue, the instrument being coated with flesh or tissue, the instrument being coated over at least a portion of the predetermined region by a coating consisting essentially of diamond of a thickness permitting transmission of radio-frequency electrical energy from the first predetermined region through the diamond coating to flesh or tissue by capacitive coupling.

4 Claims, 1 Drawing Sheet

CAUTERY MEDICAL INSTRUMENT

This application is a continuation of application Ser. No. 08/200,541, filed Feb. 22, 1994, now U.S. Pat. No. 5,699,926 which in turn is a continuation of application Ser. No. 07/991,974, filed Dec. 17, 1992, now abandoned.

DESCRIPTION OF THE PRIOR ART

This invention relates to medical instruments, and more particularly to those which are adapted for use in circumstances in which an electrical current is passed through the instrument to contact flesh or tissue.

Electrically activated instruments, commonly called cautery instruments, are known in the art and include coagulation forceps, suction cautery devices, laparoscopic electrodes, and electrode cautery tips, the last noted including ball-tip, needle, extended and flat blade electrodes. These various types of medical instruments are employed in procedures that involve cutting and/or other contact with flesh or exposed tissue. Thus, for example, surgical blade electrodes are utilized to cut through tissue, and such cutting often results in substantial bleeding. Such bleeding may interfere with successful completion of the procedure and must be controlled or terminated. Accordingly, electrical current is utilized to cauterize the exposed tissue. For this purpose, the blade electrodes are affixed to handpieces which have means can De activated for passing electrical energy into the blade to cause it to transmit radio-frequency electrical energy therefrom to the flesh or tissue and cauterize. The same is true for other electrical devices noted above. However, in the process of cauterization, the problem of sticking of charred or otherwise cauterized tissue and blood to the medical implement has arisen. Such sticking is troublesome and even where not threatening the success of the procedure, is annoying and time-consuming requiring frequent cleaning of the medical instrument for proper usage.

Various proposals have theretofore been advanced for solving the problem of tissue sticking on such electrosurgical devices. Thus, for example, various coatings have been proposed for adherence to these medical instruments so as to render the surfaces less adherent, but none are entirely satisfactory. These include among others, (1) coating the entire working surface with a non-stick plastic to transmit the electrical energy by capacitive coupling (2) coating a part of the working surface with a non-stick plastic and (3) applying a non-stick plastic coating which includes islands of metallic material or metallic material embedded therein to assist in electrical conductivity. Coating the entire surface with a very thin coating to utilize capactive coupling is most satisfactory in terms of non-adherence, but has resulted in dulling cutting edges. Also, the coating will not withstand repeated usage, and can possibly degrade over time. Coating only a part has resulted in the same defects and also in charring and sticking on the uncoated part. Applying coatings with island of metal in non-stick material has nonetheless resulted in excessive charring and sticking. Moreover, some such coatings have involved complex production procedures and unsatisfactory performance. There is also the problem with some non-stick plastic coating of flaking-off to some extent which can be deleterious to the person or animal being treated.

The proposals of the prior art in some instances have brought an improvement in reducing the amount of charring of tissue and adherence to cautery instruments. However, it has been necessary to coat essentially the entire surface that comes into contact with the flesh or tissue and the like or not exceed a low level of metallic islands in order to achieve an acceptable level of charring and adherence. Moreover, the addition of a coating which completely eliminates metallic contact with tissue resulted in some undesired dulling of these electrosurgical instruments which are also used for cutting.

Although, according to some prior proposals, most, but not all, of an electrosurgical blade was covered, leaving but a minor portion exposed at an edge, this has brought about sticking and charring of tissue at the edge, obviously an undesirable result.

BRIEF DESCRIPTION OF THE PRESENT INVENTION

The present invention overcomes the problems of the prior art and provides coated cautery instruments to which coating there is substantially no adherence of charred tissue during cauterization, which coating will not degrade or dissipate over time, which coating can withstand repeated cleaning and use (such as sterilization and subsequent reuse), which coating is stable and biocompatible, which coating is extremely smooth and slick, and which coating will permit transmission of electrical energy therethrough to flesh or tissue by capacitive coupling.

Briefly, the present invention comprises a cautery instrument comprising a first predetermined region for contact with flesh or tissue, said instrument being coated over at least a portion of said predetermined region by a coating consisting essentially of diamond, said diamond coating being of a thickness permitting transmission of radio-frequency electrical energy from said first predetermined region through said diamond coating to flesh by capacitive coupling.

DETAILED DESCRIPTION OF THE INVENTION

While the invention is applicable to any cautery instrument that comes into contact with flesh, tissue, and the like, such as coagulation forceps, suction cautery devices, needle and extended needle electrodes, various ball electrodes, angled and extended blade electrodes, and other laparoscopic electrodes (including J hook, L hook, curved 30° angle, spatula, and the like) electrode cautery devices, it will be particularly described in connection with blade electrodes which are used for cutting and coagulation (cauterizing). Also, as used herein the term "working surface" means the portion of the instrument meant to come into contact with the flesh, tissue, and the like.

Figure 1:
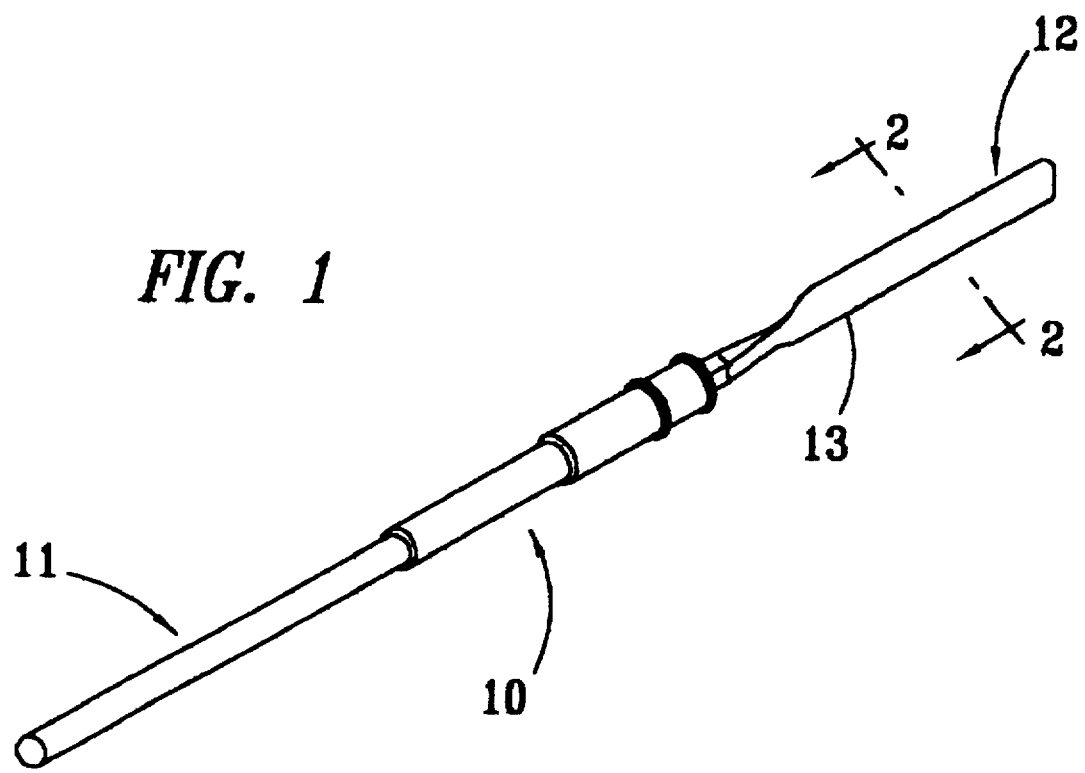
FIG. 1 is a perspective view of a cautery blade electrode which has been coated in accordance with the principles of the invention.

Now turning to the drawings and more particularly to FIG. 1 thereof, it will be observed that there is therein disclosed an electrosurgical flat blade electrode 10 having a proximal end 11 for insertion into a handle and working surface 12. The exterior of working surface 12 has coating 13 thereon. Not shown is the conventional handle, usually referred to as a "pencil" into which the blade is inserted for use, which handle has means enabling electric current to flow to the blade to permit cauterizing when desired by the user.

As known to those skilled in the art, in such blades, the characteristic of cleanliness (freedom from adherent tissue) is highly essential. Moreover, it is important to the successful use of the cautery blades that the blade remain clean and that it not be impeded by the adherence of any substance (such as blood, tissue, and the like) which may stick to the blade when it is in the coagulation (cauterizing) mode as this may retard or interfere with its use either to cauterize or to cut. This is also for other cautery instruments.

Surgical implements such as that depicted in FIG. 1 are typically formed from stainless steel or other similar non-corrosive materials. Although the principles of the invention are applicable to such blades and other electrosurgical implements made of such material, it has been found that the instruments may be of other substances such as, for example, brass, nickel, aluminum, other types of steel, or alloys. The principles of the invention may also be employed with non-metallic conductive substances provided that they possess the inherent qualities of stability and integrity sufficient to meet the desired requisites; i.e., certain conductive plastics.

The key aspect of the invention is the coating applied to at least the working surface of the electrosurgical instrument. It must be a diamond coating.

Diamond is durable and can be roughly handled and sterlized for reuse many times. This is advantageous in many countries in the world where costs are such that cautery instruments, such as blade electrodes, must be reused and cannot be disposed of after a single surgical use as is common in the United States. Further, diamond will not degrade or dissipate over time even in the form of a thin film, it is extremely smooth, it is biocompatible, and is an excellent electrical insulator. While it is also a good conductor of heat, its use as a very thin film as in the instant invention minimizes heat build-up in the diamond layer to preclude any possibility of adhesion to the diamond coated surface of charred tissue and the like and to insure that the radio-frequency electrical energy is transmitted from the conductive substrate through the diamond coating to the flesh or tissue substantially exclusively by capacitive coupling.

The thickness of the coating is not critical; it is only necessary that the coating be of a thickness sufficient to provide the desired non-stick characteristics without impeding the desired electrical characteristics; i.e., transmission of the electrical energy to the flesh or tissue by capacitive coupling; preferably, substantially exclusively by capacitive coupling. Ordinarily, a thickness of about 50 to 500 microns is suitable, with a thickness of 100 to 250 microns being optimum.

The process of coating the working surface does not form a part of the instant invention. However, a most suitable process for forming the diamond coating is by chemical vapor deposition, a well-known process for coating. Basically, a hydrocarbon such as such as methane or a chlorofluorocarbon is decomposed into a hot plasma which deposits diamond on the substrate which has previously been heated to about 350 to 850° C. or higher. The coating, a very thin film, of diamond is distributed substantially uniformly on the substrate. It will be understood that the diamond coating may contain minor amounts of impurities, such as carbon, without adversely affecting its performance.

If chemical vapor deposition is used it may be necessary in some instances to pretreat the working surface to enable satisfactory deposition of the diamond film thereon. For example, it is difficult to adhere the diamond to stainless steels which contain high levels of cobalt. In such cases an intermediate conductive layer to which the diamond will readily adhere is first adhered to the stainless steel by any contentional technique such as sintering, plating and the like. Such intermediate layer can be any metal which adheres to stainless steel and to which the diamond can be applied by chemical vapor deposition.

Figure 2:
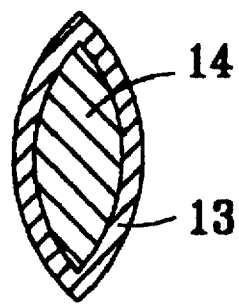
FIG. 2 is a sectional view along line 2—2 of FIG. 1.

This is best illustrated in FIG. 2 which shows underlying blade substrate 14 with coating 13 consisting of diamond. It is preferred to coat the entire portion of the blade which is to come into contact with the flesh or tissue, although in some instances an edge of the blade or some other portion thereof that may, but does not ordinarily come into contact with the flesh or tissue, may be left uncoated. This is true with respect to other cautery instruments.

It will now be evident that there has been described herein an improved medical instrument. Although the inventive concepts hereof have been illustrated by way of a preferred embodiment, it will be evident to those skilled in the art that other adaptions and modifications may be employed without departing from the spirit and scope of the inventions.

The terms and expressions used herein are employed as terms of description and not of limitation; and consequently, there is no intent in the use thereof of excluding any and all equivalents, but on the contrary, it is intended to include all adaptations and modifications that may be employed without departing from the spirit and scope of the invention as defined in the claims.

What is claimed is:

1. A cautery instrument comprising a first predetermined region for contact with flesh or tissue, said instrument being coated over at least a portion of said predetermined region by a coating consisting essentially of diamond permitting transmission of radio-frequency electrosurgical energy from said first predetermined region through said diamond coating to flesh or tissue principally by capacitive coupling, said diamond coating having a thickness of at least one micron.

2. The cautery instrument of claim 1 wherein said predetermined region is completely coated with said coating.

3. The cautery instrument of claim 1 wherein said coating consists of diamond.

4. The cautery instrument of claim 2 wherein said coating consists of diamond.

* * * * *